(12) United States Patent
Karssemeijer et al.

(10) Patent No.: US 9,289,183 B2
(45) Date of Patent: Mar. 22, 2016

(54) INTERACTIVE DISPLAY OF COMPUTER AIDED DETECTION RESULTS IN COMBINATION WITH QUANTITATIVE PROMPTS

(75) Inventors: Nico Karssemeijer, Beek-Ubbergen (NL); Shih-Ping Wang, Los Altos, CA (US)

(73) Assignee: QVIEW MEDICAL, INC., Los Altos, CA (US)

( * ) Notice: Subject to any disclaimer, the term of this patent is extended or adjusted under 35 U.S.C. 154(b) by 584 days.

(21) Appl. No.: 13/512,164

(22) PCT Filed: Nov. 27, 2009

(86) PCT No.: PCT/US2009/066020
§ 371 (c)(1),
(2), (4) Date: Nov. 9, 2012

(87) PCT Pub. No.: WO2011/065950
PCT Pub. Date: Jun. 3, 2011

(65) Prior Publication Data
US 2013/0050239 A1     Feb. 28, 2013

(51) Int. Cl.
*A61B 6/00* (2006.01)
*G06F 19/00* (2011.01)
*G06T 7/00* (2006.01)

(52) U.S. Cl.
CPC ............... *A61B 6/469* (2013.01); *A61B 6/502* (2013.01); *G06F 19/321* (2013.01); *G06T 7/0014* (2013.01); *G06T 2200/24* (2013.01); *G06T 2207/20104* (2013.01); *G06T 2207/30068* (2013.01)

(58) Field of Classification Search
CPC ............... G06T 11/001; G06T 7/0012; G06T 2207/10081; G06T 2207/10116; G06T 2207/30068; G01N 23/046
See application file for complete search history.

(56) References Cited

U.S. PATENT DOCUMENTS 6,058,322 A     5/2000  Nishikawa et al.
6,266,453 B1 *  7/2001  Hibbard ................ G06T 3/0006
                                                                          382/131
(Continued)

FOREIGN PATENT DOCUMENTS

WO     WO2008050332 A2    5/2008

OTHER PUBLICATIONS

Karssemeijer et al. Computer-aided detection versus independent double reading of masses on mammograms. Radiology, 227(1): 192-200, 2003.

(Continued)

*Primary Examiner* — Antonio A Caschera
(74) *Attorney, Agent, or Firm* — William L. Wang

(57) ABSTRACT

Methods and related systems provide an interactive user interface in which CAD results are displayed in such a way that they may be used for both interpretation of detected abnormalities and for avoiding perceptual oversights. The output of a (multi-view) computer aided detection system is presented to the reader of a screening case in two phases: (1) an interactive phase, and (2) a prompting phase. In the first phase the reader can probe image locations for CAD information. In the second phase regions identified as relevant by the CAD system and not yet probed by the reader are prompted or displayed to the user, as these may have been overlooked by the reader. The CAD results can be calibrated to a probability of malignancy.

19 Claims, 7 Drawing Sheets

(56) References Cited

U.S. PATENT DOCUMENTS

| | | | |
|---|---|---|---|
| 6,628,815 B2 | 9/2003 | Wang | |
| 7,184,582 B2 | 2/2007 | Giger et al. | |
| 7,418,119 B2 | 8/2008 | Leichter et al. | |
| 7,466,848 B2 | 12/2008 | Metaxas et al. | |
| 7,597,663 B2 | 10/2009 | Wang et al. | |
| 2005/0234570 A1 | 10/2005 | Horsch et al. | |
| 2006/0018548 A1 | 1/2006 | Chen et al. | |
| 2007/0014454 A1* | 1/2007 | Sawyer et al. | 382/128 |
| 2007/0036402 A1* | 2/2007 | Cahill | G06T 7/0012 382/128 |
| 2007/0081712 A1 | 4/2007 | Huang et al. | |
| 2008/0107323 A1 | 5/2008 | Ratner et al. | |

OTHER PUBLICATIONS

Karssemeijer et al. Computer aided detection of masses in mammograms as decision support. Br J Radiol, 79 Spec No. 2:S123-6, 2006.

Karssemeijer et al. An interactive computer aided decision support system for detection of masses in mammograms. In E A Krupinski, editor, Digital Mammography, LNCS 5116, pp. 273-278. Springer, 2008.

Yankaskas et al., Association of Recall Rates with Sensitivity and Positive Predictive Values of Screening Mammography, American Journal of Roentgenology 2001, vol. 177, pp. 543-549.

Van Engeland et al. Matching breast lesions in multiple mammographic views. Medical Image Computing and Computer-Assisted Intervention, LNCS 2208, pp. 11 72-1173. Springer, 2001.

Paquerault et al. Improvement of computerized mass detection on mammograms: fusion of twoview information. Med Phys, 29(2):238-47, Feb. 2002.

Van Engeland et al. Finding corresponding regions of interest in mediolateral oblique and craniocaudal mammographic views. Med Phys, 33(9):3203-12, 2006.

Van Engeland et al. Combining two mammographic projections in a computer aided mass detection method. Med Phys, 34(3):898-905, 2007.

Timp et al. A regional registration method to find corresponding mass lesions in temporal mammogram pairs. Med Phys, 32(8):2629-38, 2005.

* cited by examiner

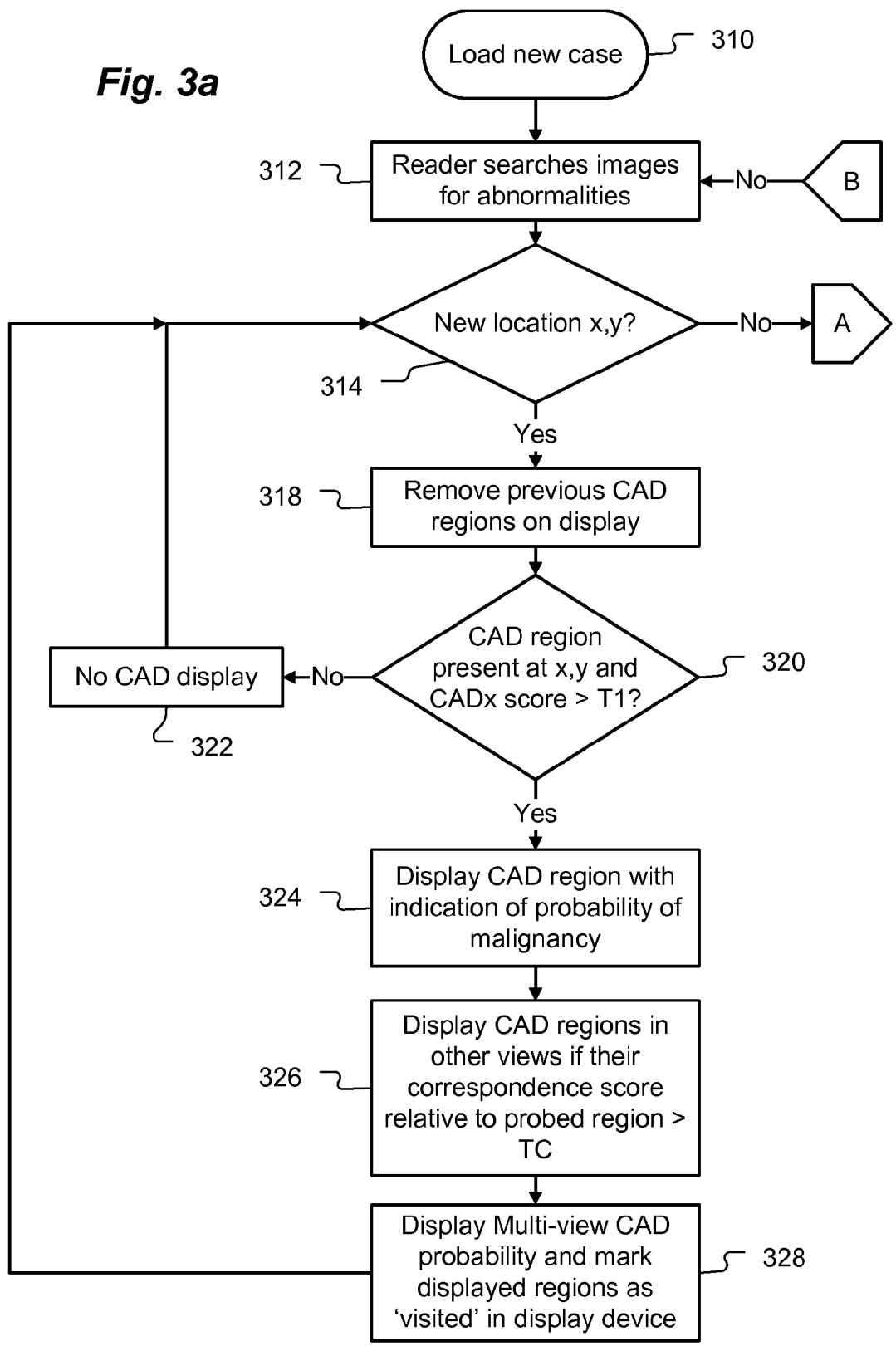

INTERACTIVE DISPLAY OF COMPUTER AIDED DETECTION RESULTS IN COMBINATION WITH QUANTITATIVE PROMPTS

BACKGROUND

1. Field

This specification relates to medical imaging systems and processes. In particular, the present invention relates to the computer aided detection of breast malignancies, and devices and methods of interactive display of computer aided detection results in combination with quantitative prompts.

2. Related Art

Current systems for computer aided detection (CAD) are aimed at avoiding that radiologists miss abnormalities due to perceptual oversights during a radiological screening examination. In these systems potentially abnormal patterns identified by computer programs are displayed after the reader has inspected a screening case. Readers are encouraged to evaluate regions marked by CAD in addition to the ones they identified themselves as suspicious. On the other hand, decisions with respect to regions they already inspected are not to be changed.

A second source of observer errors in radiological screening is related to misinterpretation of detected abnormalities. However, this type of error is not addressed in current CAD prompting systems. In previous work it has been shown that there is a potential to use current CAD systems for improvement of interpretation of mammographic masses. See, N. Karssemeijer, J. D. Otten, A. L. Verbeek, J. H. Groenewoud, H. J. de Koning, J. H. Hendriks, and R. Holland. Computer-aided detection versus independent double reading of masses on mammograms. Radiology, 227(1): 192-200, 2003. In fact, if analysis is restricted to regions that are considered suspicious by radiologists, malignancy ratings of a CAD system were shown to be comparable in quality to assessments of experienced radiologists. See, N. Karssemeijer, J. D. Often, H. Rijken, and R. Holland. Computer aided detection of masses in mammograms as decision support. Br J Radiol, 79 Spec No 2:S123-6, 2006. Therefore, combining CAD ratings with radiologists' assessments can lead to significant improved detection performance, and that this improvement may be comparable to that obtained by independent double reading. See, Id.

However, independent combination of CAD ratings with reader scores is not likely to become accepted in screening practice. Moreover, it may be expected that readers will benefit more from CAD can if they learn to use it interactively. See, N Karssemeijer, A Hupse, M Samulski, M Kallenberg, C Boetes, and G den Heeten. An interactive computer aided decision support system for detection of masses in mammograms. In E A Krupinski, editor, Digital Mammography, LNCS 5116, pages 273-278, 2008, hereinafter "Digital Mammography 2008." This is especially true if they are aware of the limitations of the CAD system.

A third source of observer errors in radiological screening is a lack of quantitative matrix or guideline to determine which patient should be recalled for a more in-depth "diagnostic" examination. The current standard BIRADS system, used in radiological examinations, supplies a guideline specifying that no recall is necessary for "probably benign" cases, or BIRADS category III cases. It further specifies that these BIRADS III cases have a risk of malignancy below 2% (two percent), but it gives no quantitative guideline on how to assess that a lesion is below 2% in probability of malignancy. This vagueness results in a wide specificity range in the practice of radiologists in making recalls during screening. For example, see the report by Yankaskas et al, in American Journal of Roentgenology 2001, vol. 177, pages 543-549, entitled "Association of Recall Rates with Sensitivity and Positive Predictive Values of Screening Mammography", of a study included 215,665 mammograms. The reported specificity varied from 86.6% (or 13.4% recall) to 98.1% (1.9% recall). The low specificity would result in substantially increased healthcare costs and increased anxiety in recalled patients. However, this source of errors is not addressed in current CAD prompting systems.

U.S. Application Publication No. 2004/0184644 discusses a display for computer aided evaluation of medical images in the diagnostic phase rather than at the screening phase. Also, although a method is described as displaying a likelihood of malignancy, the likelihood appears to be relative only and there is no discussion of calibration to absolute or quantitative probabilities.

SUMMARY

According to some embodiments, a method of interactively displaying computer aided detection results of medical screening images, such as screening mammograms, is provided. The method includes receiving a digitized screening image of a living tissue, such a breast tissue, and processing the image using one or more computer aided detection algorithms thereby generating computer aided detection results. The digitized image is displayed to a user. One or more locations of user identified regions of interest are received, that are identified by the user as possibly relating to an abnormality, such as a malignancy, in the tissue. In response to the received location from the user, information is displayed to the user relating to a likelihood of an abnormality (where malignancy is a specific abnormality) of the user identified region of interest based on the computer aided detection results. The computer aided detection results can be related to a quantitative probability of an abnormality, in some embodiments using a calibration procedure including a number, such as 1000 or 5000, or more, of test images known to include an abnormality. The information relating to a likelihood of all abnormalities in any image to be viewed are preferably pre-calculated. Upon the receipt of location of the user activated region of interest, an abnormality is preferably displayed in "real-time" interactively to the user in response The information displayed to the user relating to the likelihood, or quantitative probability, of an abnormality can include a numerical and/or graphical indicator of the probability of an abnormality corresponding to the user identified region of interest.

The system can also simultaneously display a second digitized screening image of the living tissue, such as from a prior year or from a different view, and automatically display information relating to a likelihood of an abnormality in the second digitized image in response to the received location of the user identified region of interest.

The computer aided detection results preferably include one or more computer identified regions of interest identified by the algorithm as possibly relating to an abnormality. The system can keep track of and preferably mark user identified regions displayed during the reading of a case, and can restrict display of traditional CAD prompts before closing a case to regions not yet identified by the reader.

Further features and advantages will become more readily apparent from the following detailed description when taken in conjunction with the accompanying drawings.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 3*a*-*b* is a flowchart showing steps involved in the displaying CAD results to a user, according to some embodiments.

DETAILED DESCRIPTION OF THE PREFERRED EMBODIMENTS

Figure 1:
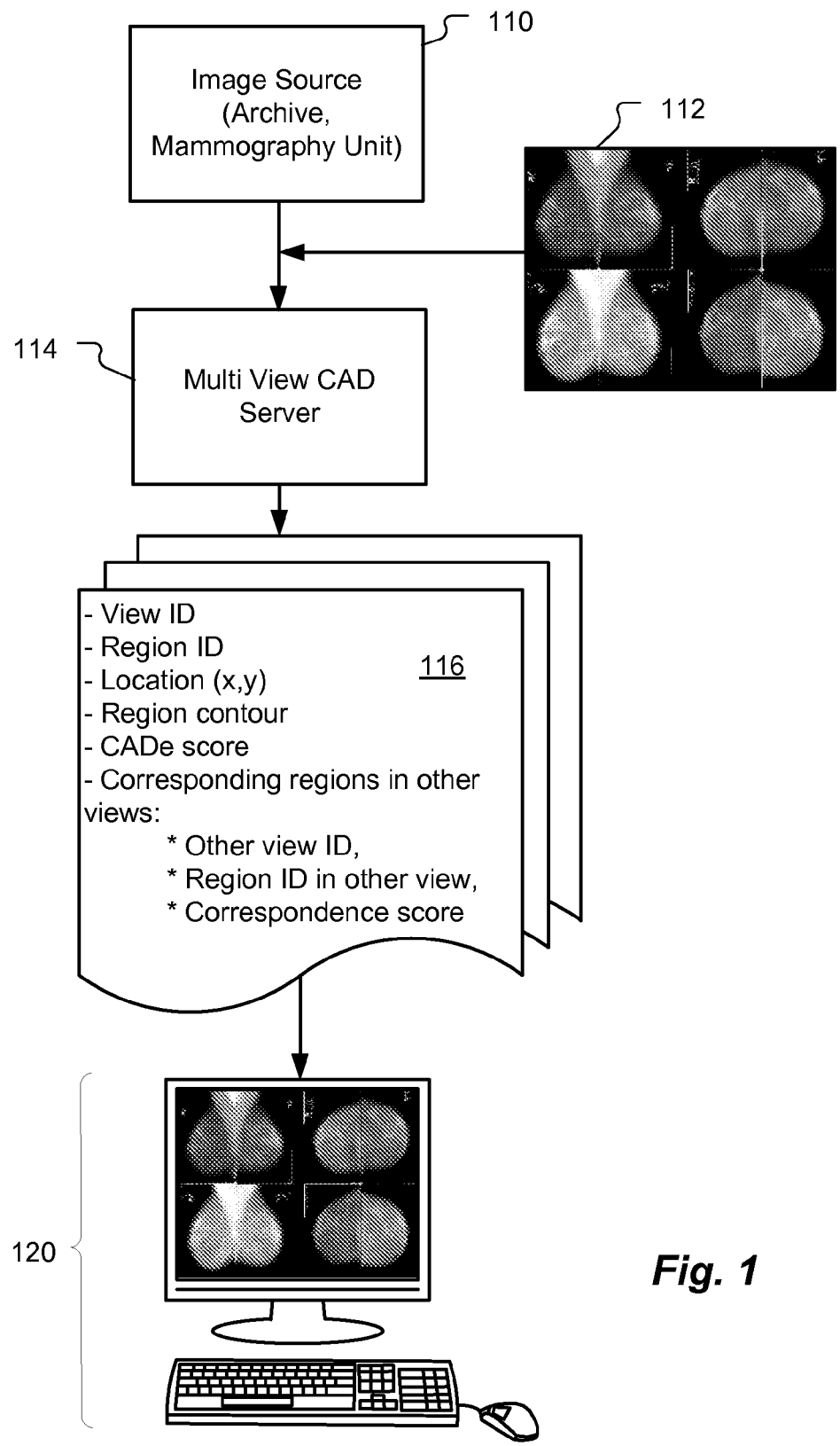
FIG. 1 shows a schematic of a system for interactively displaying CAD results in combination with prompts, according to some embodiments.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, a user interface is provided in which CAD results are displayed in such a way that they may be used for both interpretation of detected abnormalities and for avoiding perceptual oversights. A system is provided in which the output of a (multi-view) computer aided detection system is presented to the reader of a screening case in two phases: (1) an interactive phase, and (2) a prompting phase. In the first phase the reader can probe image locations for CAD information, as described in Digital Mammography 2008, which is incorporated herein by reference. In the second phase regions identified as relevant by the CAD system and not yet probed by the reader are prompted or displayed to the user, as these may have been overlooked by the reader.

According to some embodiments, in the interactive phase, all image locations in a multiview case that correlate with the probed location are displayed simultaneously (using CAD computed correspondence). Apart from, or instead of, malignancy ratings computed at each of the individual locations, an overall probability of malignancy may be presented to the reader, which combines information from all views in a supervised classifier.

According to some embodiments, the probability of malignancy/disease for single image locations or combined locations from multiple views are computed by applying the CAD system to a large database of representative cases with known pathology. In other words, the relative output of the CAD system is transformed, or calibrated, to a statistical probability using the database. Taking prevalence of the disease into account in a Bayesian scheme, a quantitative and unbiased estimate of the probability that a disease is present is obtained. According to some embodiments, this probability is presented to the reader who can use it to make a final decision. More details and an example are given below.

FIG. 1 shows a schematic of a system for interactively displaying CAD results in combination with prompts, according to some embodiments. A multi-view CAD server 114 processes screening medical images an example of which is shown as image 112 from an image source 110 such as an archive or a mammography unit. CAD server 114 preferably process the medical images in a standalone, that is, without user input.

The CAD results 116 include locations in images with descriptors. These descriptors may include a region boundary, an assessment of the probability that the region is abnormal (e.g. cancer), and/or measures indicating correspondence of the region with regions detected in other views from the same object (images from other angles, previous images of the same patient, etc). A display system 120 loads images and CAD results 116 of a patient. Since CAD server 114 has preferably calculate the probability assessments and related information ahead of time, in a standalone manner, the display system 120 is able to display the probability results in real-time and interactively in response to the user's probes or queries.

Figure 2A:
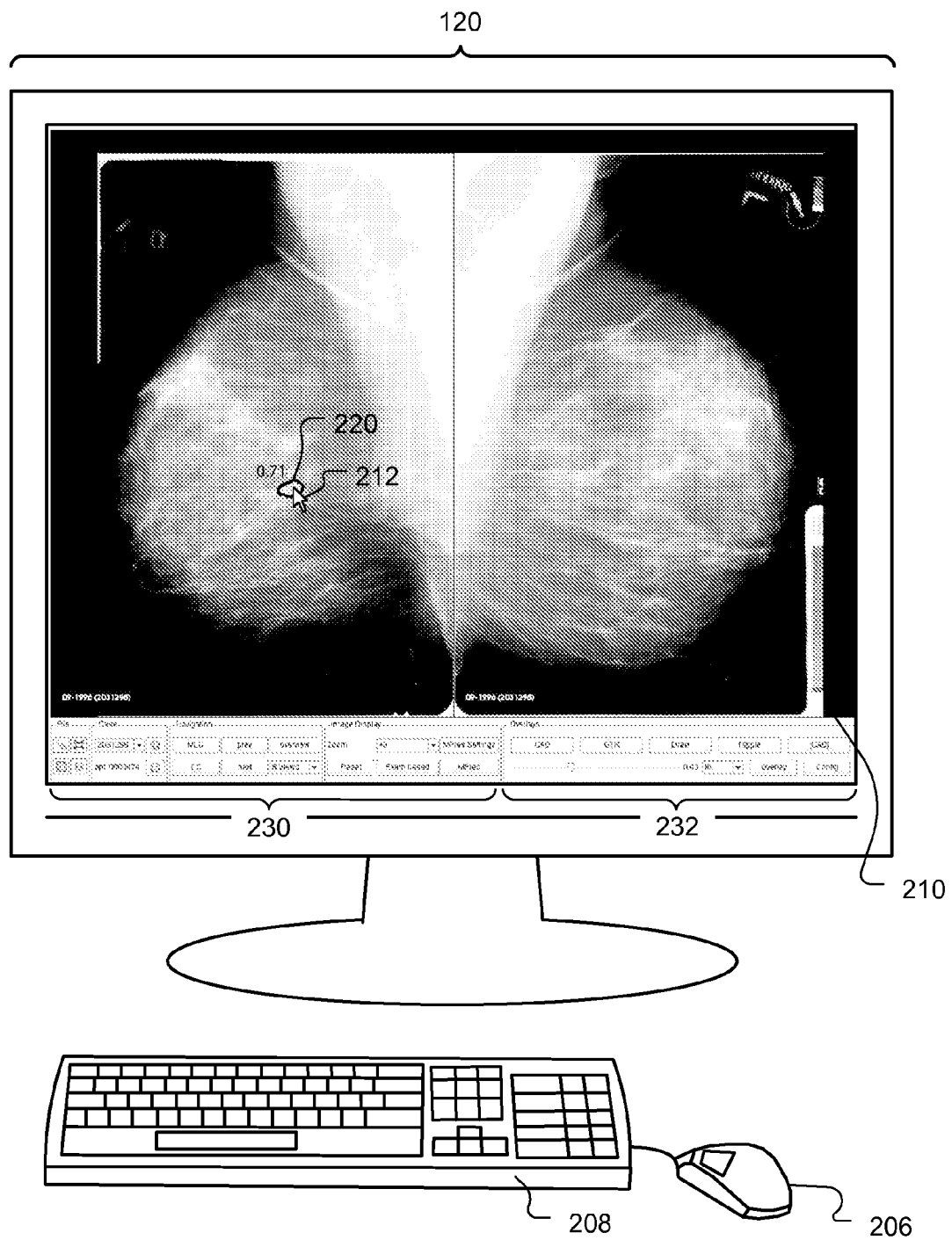
FIGS. 2*a*-*d* show an example of a radiologist workstation with an interactive CAD display, according to some embodiments.

FIGS. 2*a*-*d* show an example of a radiologist workstation with an interactive CAD display, according to some embodiments. The display screen 210 corresponds to a display screen in display system 120 described in FIG. 1. As shown in FIG. 2*a*, the display system 120 also includes a keyboard 208 and a pointing device 206 that controls a pointer 212 on screen 210. According to some embodiments, other methods of user input are provided such as a track ball, trackpad or screen 210 can be a touch sensitive display.

According to some embodiments, the user interface of the display system 120 allows the user, for example a radiologist, to query (or probe) a location in the image for CAD results. If CAD results are present at the requested location and if the probability computed by the CAD system exceeds a predetermined threshold T1, the CAD results are displayed. For example, a radiologist finds a suspicious location and therefore probes for CAD results by clicking on region 220 with pointer 212. For further details of interactive procedures according to some embodiments, see FIGS. 3a-b.

According to some embodiments, the display system 120 displays the contour of the CAD detected lesion. As shown in the example of FIG. 2a, the contour of region 220 is displayed. According to some embodiments the display 120 may include a numerical display. As shown in the example of FIG. 2a, the numerical probability of malignancy of 0.71 is displayed adjacent region 220. According to some embodiments a graphical (e.g. color) indicator of the probability that the region is a cancer (or other abnormality searched for) is displayed. In the example shown in FIG. 2a, the color of the region boundary and/or the color of the numerical value can correspond to certain predetermined ranges for probabilities of malignancy. According to some embodiments a probability of malignancy of less than 2% is displayed as green; a probability of between say 2% and 5% is displayed as yellow; a probability of between say 5% and 40% is displayed as orange; and a probability of greater than 40% is displayed as red. The color scale can also be a continuum. The marker size or shape could also be used as indicators of probability.

According to some embodiments, one or more of the features of the display system 120 such as numerical display, graphical display, and contour display can be set by the user and/or by an administrator. For example, the numerical ranges corresponding to the graphical color displayed can be set the user or by an administrator.

Figure 2B:
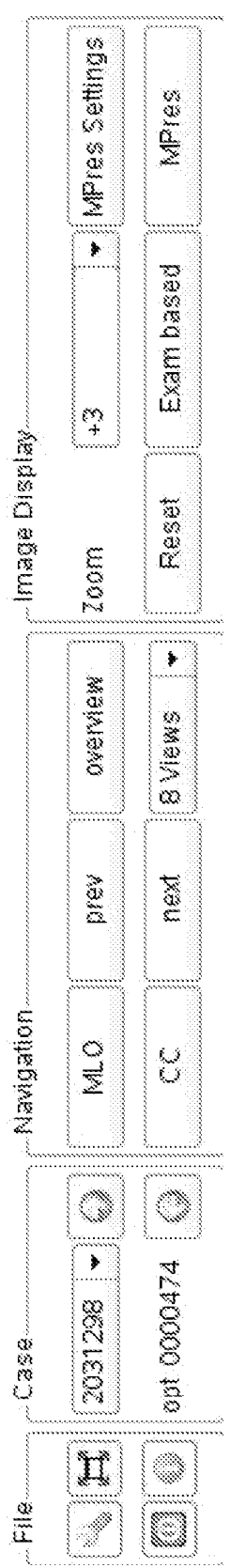
Figure 2C:
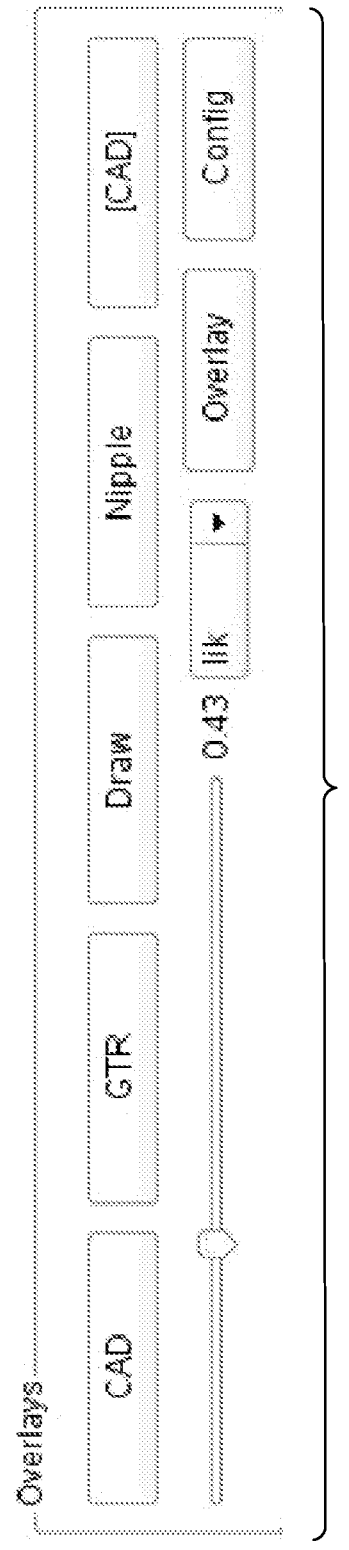

FIGS. 2b and 2c show greater detail of some of the on-screen control regions 230 and 232 that can be controlled by the user using pointer 212 controlled by pointing device 206 (or, for example, by touch sensitive display).

Figure 2D:
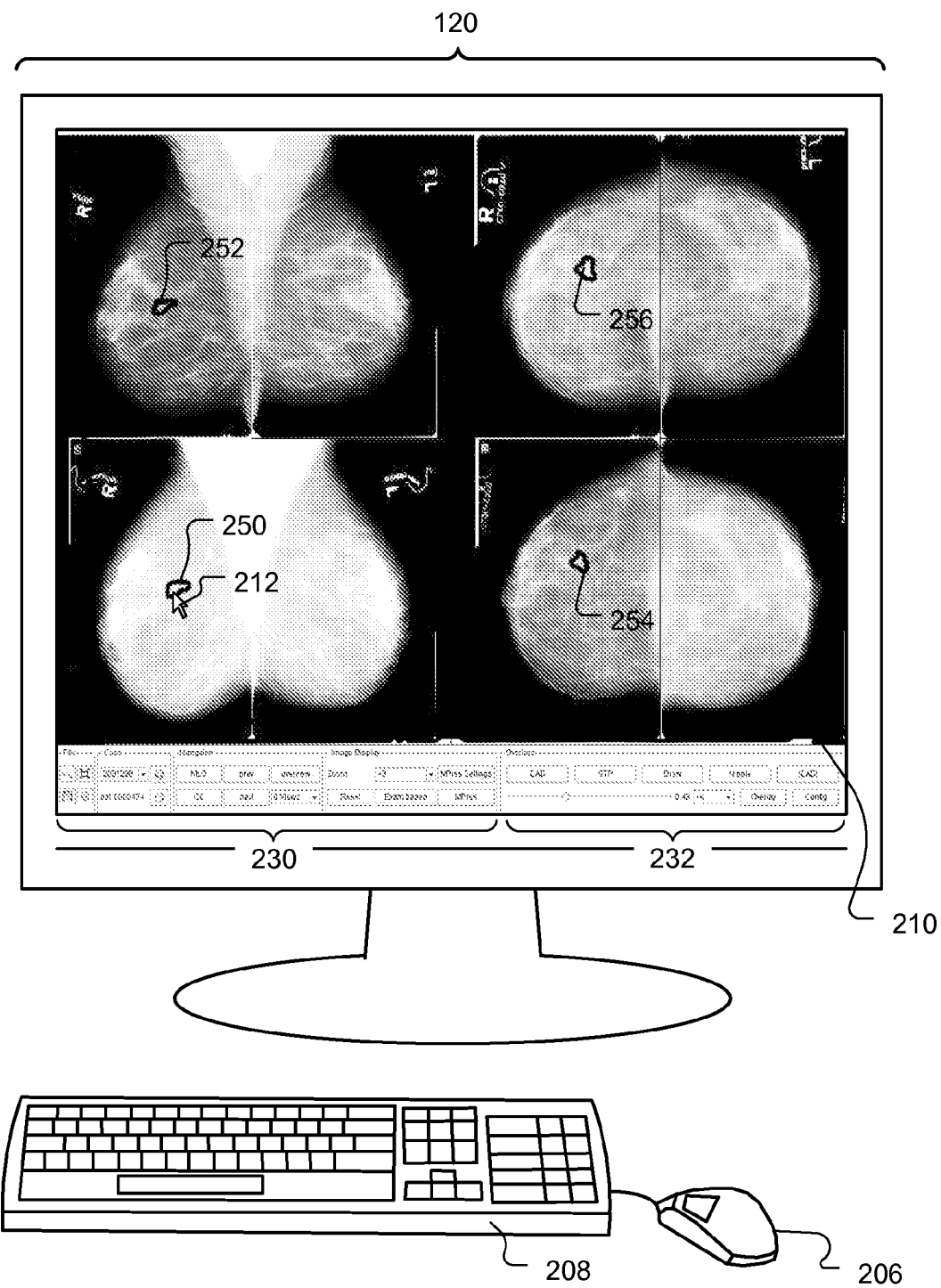

FIG. 2d shows screen 210 in a multi view mode for screening mammography. The lower four images are the present case images, and the upper four images are from a prior year of the same patient. The images on the left half are MLO images and the images on the right half are CC images. According to some embodiments, the display system 120 includes simultaneous display of corresponding lesions in other views, in cases such as shown in FIG. 2d, where multiple views of the same object (breast) are present. The user selects a suspicious region 250 using pointer 212 on the right MLO current mammogram. In response, the display system 120 displays, via contour in this example, corresponding regions 252, 254 and 256 in three of the other images, as shown. The correspondence is preferably determined by thresholding a correspondence score computed by the CAD system. In this way the user has to probe only once to obtain all information computed by the CAD system regarding the probed lesion. According to some embodiments, corresponding lesions are only shown if the CAD computed correspondence score exceeds a threshold TC. See the flowchart of FIGS. 3a-b for further details.

According to some embodiments, the display system 120 may display an overall estimate of probability of malignancy based on available information from all views of the lesion.

According to some embodiments, the presence of a CAD mark at the probed location can be determined by computing the distance of the probed location to the location of the CAD region, and by requiring that this distance is smaller than a predetermined threshold. According to some embodiments, the display system may also require that the location is inside the region detected by CAD, or within some distance from its boundary.

According to some embodiments, the display system 120 keeps track of the locations probed by the user and the CAD regions that are displayed. When the reader has completed inspecting the case he/she may request display of traditional CAD marks to check if no abnormalities were missed. This portion of the display is similar to a conventional CAD interface. However, instead of displaying all CAD marks exceeding a predetermined threshold (e.g. see threshold T2 in FIG. 3b), the display system checks whether regions were already displayed during the interactive phase. Only CAD marks that were not probed by the reader are displayed. This will dramatically reduce the number of false positives and avoids forcing readers to check the same CAD regions twice.

Figure 3B:
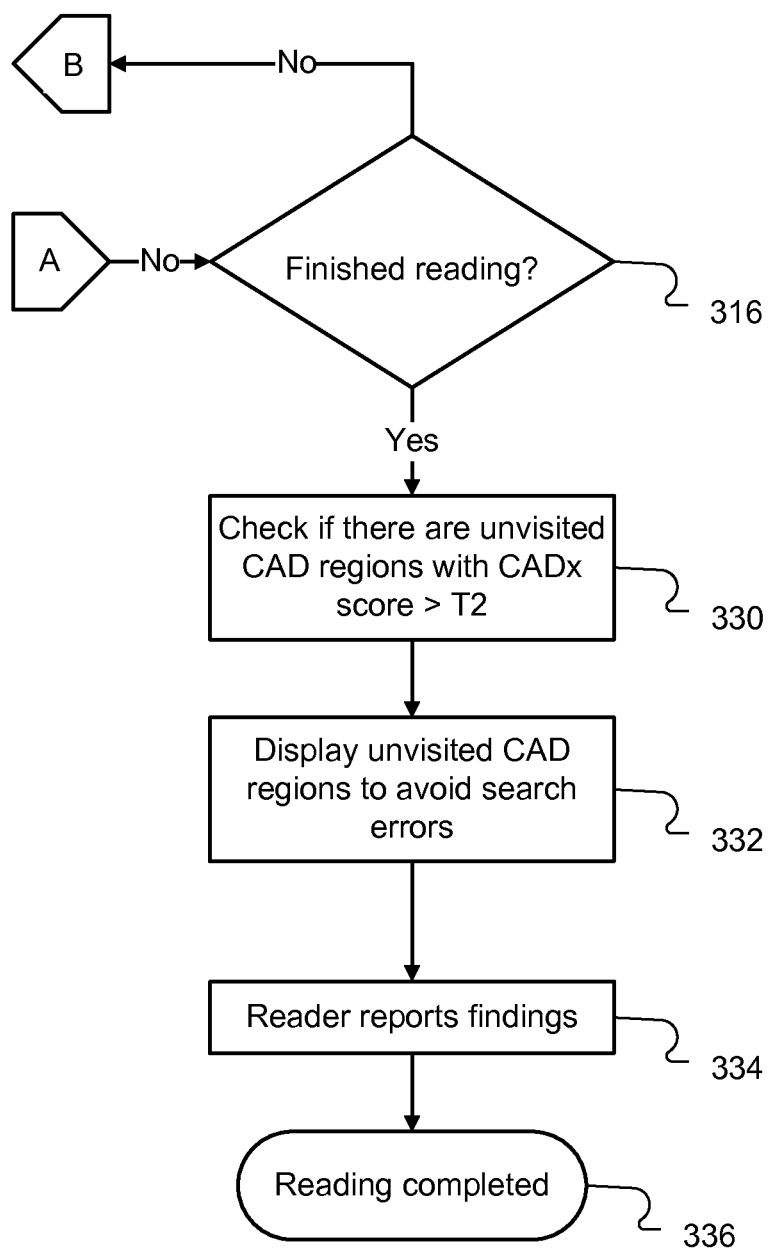

FIGS. 3a-b are a flowchart showing steps involved in the displaying CAD results to a user, according to some embodiments. In step 310 a new screening case is loaded. In step 312 the reader, for example a screening radiologist, searches the images of the case for abnormalities and select a location, for example by clicking a pointer on the location having coordinates x,y. In step 314, a decision is made, if the selected location is a new location then control passes to step 318. If the location is not new, control passes to step 316. In step 318, for a new location, the previous CAD regions being displayed, if any, are removed. This is preferable to avoid clutter and confusion by the user due to more than one CAD result being displayed simultaneously. In step 320 a decision is made whether there is a CAD region present at the location x,y, and if so, is the score or rating (also referred to as the CADx score, or the CADe score) greater than a predetermined threshold T1. If there is no corresponding CAD region or if the CADx score is less than or equal to the threshold T1, then in step 322 not CAD is displayed and the display system waits for further user input in step 312.

If the location x,y corresponds to a CAD region with an score above threshold T1, than in step 324 the CAD region is displayed to the reader along with an indication of the probability of malignancy. According to some embodiments the indication includes information relating to the probability of malignancy. For example different colors can be used to represent different probability ranges, and or the probability can be directly displayed. To obtain the probability values from the CADx score, a calibration method is preferably used as is described in further detail below. According to some embodiments, the probabilities of malignancy for each CAD region is calculated ahead of time by the CAD server, so as to provide for display of the corresponding lesions in real-time in an interactive fashion.

Note that even though BIRADS category III cases are specified as less than 2% probability of malignancy, users of conventional CAD systems typically have no way to asses whether a given ROI is less than 2%. Thus, it is very difficult for such users to make judgements and therefore can be quite arbitrary. Because of the uncertainty, many users tend to over-estimate the probability, which substantially reduces user's specificity and greatly increases the false positive rate. Thus, providing a quantitative calibration such as described herein will increase the user's specificity an reduce the false positive rate. As a result, the calibration can greatly reduce overall costs associated with the screening procedure, as a well as decrease stress and anxiety on patients by reducing recalls.

In step 326, the display system displays CAD regions in other views if their correspondence score relative to the probed region is greater than a threshold TC. The same lesion may be present in multiple images (or views) of an organ. For instance, in screening mammography lesions are often seen in CC and MLO projections of the breast, and they may be visible in prior mammograms. The interactive CAD display system is aimed at minimizing user interaction required, to make reading more efficient. To this end, according to some embodiments, the system uses automated image analysis methods to establish correspondence between lesions in multiple views. Such methods have been described in the literature where the aim of research was improvement of CAD detection performance. See, e.g. S. van Engeland and N. Karssemeijer. Matching breast lesions in multiple mammographic views. In W Niessen and M Viergever, editors, Medical Image Computing and Computer-Assisted Intervention, LNCS 2208, pages 1172-1173. Springer, 2001; S. Paquerault, N. Petrick, H. P. Chan, B. Sahiner, and M. A. Helvie. Improvement of computerized mass detection on mammograms: fusion of two view information. Med Phys, 29(2):238-47, February 2002; S. van Engeland and N Karssemeijer. Finding corresponding regions of interest in mediolateral oblique and craniocaudal mammographic views. Med Phys, 33(9):3203-12, 2006; S. van Engeland and N. Karssemeijer. Combining two mammographic projections in a computer aided mass detection method. Med Phys, 34(3):898-905, 2007; and S. Timp, S. van Engeland, and N. Karssemeijer. A regional registration method to find corresponding mass lesions in temporal mammogram pairs. Med Phys, 32(8): 2629-38, 2005, each of which is incorporated herein by reference. Using correspondence, the interactive CAD display can be made more efficient, as the user does not have to activate CAD in each view himself/herself. Moreover, according to some embodiments, the malignancy rating of a lesion is based on information from multiple views. According to some embodiments, the correspondence between lesions in multiple views is established ahead of time by the CAD server, so as to provide for display of the corresponding lesions in real-time in an interactive fashion.

In step 328, a multi-view CAD probability is displayed, and displayed regions are marked as 'visited' by the display system. In step 316, if the reader is finished reading control passes to step 330, in which a check is made to determine if there are any unvisited CAD regions having a CADx score of greater than a threshold T2, which is ordinarily greater (i.e. having a greater probability of malignancy) than T1. Note that according to some embodiments, threshold T2 corresponds to a threshold used by conventional CAD systems to display regions to a user. In step 332, any unvisited CAD regions having a score above T2 are displayed to the reader so as to avoid overlooked abnormalities. Note that since only unvisited regions are displayed, the reader is not forced to analyze and make dismissal decisions for any regions that he/she had already identified in step 312 as being suspicious. In step 334 the reader reports his/her findings, and in step 336, the reading is completed.

According to some embodiments the threshold T1 is related to a known standard, such as the American College of Radiology BI-RADS® Assement Categories. In particular, according to some embodiments, the threshold T1 is set to correspond to the BI-RADS® Category 3, "Probably Benign" should have a less than 2% risk of malignancy. Thus, if the probability of malignancy is calculated to be less than 2%, then it will not be displayed by the display system in response to a selection by the user. According to some embodiments, in step 322 of FIG. 3a instead of making no CAD display when the CADx score is less than T1, the display system displays a green marker to indicate to the user that the user identified region corresponds to a probability of malignancy of, for example, below 2%. It is anticipated that such information can be very useful to a reader in the determination whether to recall the patient for additional examinations such as diagnostic procedures. Especially, most if not all readers really do not know the probability of a low probability lesion. In fact, it is anticipated this process will substantially improve the reader's specificity (or substantially reduce the false positive rate) so that the specificity spread in readers will be narrowed. This will in turn reduce the healthcare costs substantially.

Further detail relating to the transformation of CAD system output to probability of malignancy will now be provided. In the interactive CAD system described herein, readers can probe image locations for information related to cancer/disease presence. The output of a CAD system is a set of locations, each with an associated malignancy/disease rating. Note that in the following description we use the term "rating," although other terms for the output score of a CAD system such as CADx score can be used, as discussed with respect to FIGS. 3a-b.

According to some embodiments, the rating can also be a combined rating for a multi view set of locations. Ratings indicate likelihood of the presence of cancer/disease. However, ratings are not probabilities in the statistical sense. Here we give an example how marker ratings can be converted to probabilities that are correct estimates of cancer/disease presence. To compute these probabilities prevalence of the disease has to be known and a large representative series of cases with known pathology has to be available. In screening programs this generally is the case.

Here we give an example of the computation for breast cancer screening using mammograms. We assume that we are dealing with mass CAD markers, but the same argument can hold for microcalcification markers or for combined markers. To compute the probability that a mass marker is a true positive (TP) as a function of marker rating we have to know the frequency in which true positive mass markers occur in a given setting. In screening, this frequency can be computed from the incidence I, the sensitivity of mammography, and the fraction of screen detected cancers associated with masses. The incidence of cancer in a screening program can be computed by adding the detection and interval cancer rate. Incidence depends on the screening interval (one or two year) and the population. In most countries good estimates of incidence are available. In Western countries incidence lies in the range of 4 to 10 per 1000 women. It is noted that not all cancers are visible in mammograms, and some are only visible as microcalcifications Suppose the rate at which cancers visible as masses in mammograms occur is known and that the rate of false positive markers of the CAD system is $r_N(T)$ per image (mammograms typically consist of 4 images, 2 views of each breast), with a threshold, T. Then, in a representative series of K mammograms the expected number of false positive CAD marks, denoted by $m_N$, is $$m_N = 4Kr_N(T).$$

In the same series the expected number of true positive CAD marks $m_A$ is $$m_A = 2Kf_AS$$

with $f_A$ the frequency of cancers visible as masses and S the sensitivity of the CAD system at $r_N$ false positives per image at the used setting of by threshold T.

Every CAD mark is associated with a marker rating l which increases (or decreases) if the likelihood that a cancer is present increases. From a series of representative training cases we can determine the conditional probability densities f(l|A) and f(l|N) of l given cancer is present (class A) or not (N). Using Bayes theorem we can derive an expression for the probability that a CAD mark with rating l is at a cancer location:

$$P(A|l) = \frac{f(l|A)p(A)}{f(l)}$$
$$= \frac{f(l|A)p(A)}{f(l|A)p(A) + f(l|N)p(N)}$$
$$= \frac{f(l|A)m_A/(m_A + m_N)}{f(l|A)m_A/(m_A + m_N) + f(l|N)m_N/(m_A + m_N)}$$
$$= \frac{f(l|A)m_A}{f(l|A)m_A + f(l|N)m_N}$$
$$= \frac{f(l|A)f_A S}{f(l|A)f_A S + f(l|N)2r_N(T)}$$
$$= \frac{f_A S}{f_A S + 2r_N(T)f(l|N)/f(l|A)}$$

In this way, the CADx score rating form the CAD system can be calibrated to the probability of malignancy.

According to some embodiments, an alternative method is provided for calibrating the CADx score rating from a given CAD system to the probabilities of malignancy. A CAD system is calibrated by applying the system to a sufficiently large number of known cancer cases were detected by mammography screening. Preferably, the cases are randomly or consecutively selected. A threshold, or the score value is determined for the CADx score at which the CAD system correctly identifies the desired set point for probability of malignancy. For example, to determine what CADx score corresponds to a 2% probability of malignancy, the threshold of CADx score that yields 100 misses out of 5000 cases is determined. According to some embodiments, this technique is repeated to find the CADx scores that correspond to other number of missed malignancies. After a suitable number of points are determined, a look up table is then generated by interpolation.

The number of cases used should be chosen such that the statistical error is acceptable for a given application. For example, for approximately 5000 randomly or consecutively selected cases and a set point of 2% probability of malignancy, statistical error is approximately 0.2%. It has been found for many applications that at least 1000 cases should be used for the described calibration procedure. More preferably about 5000 cases or more are used. Note that since the set point was calibrated using known cases detected by screening mammography, the set point represents a probability of malignancy detectable by mammography. It is known that mammography only detects a fraction of the detectable malignancy. Currently there is a consensus that mammography can detected approximately over 50% of detectable malignancies. Therefore, according to some embodiments, a more conservative calibration procedure is provided in which a factor of 2 is built into the calibration. For example for a probability of malignancy of 2%, the set point of the CADx score is determined that corresponds to 1% probability of malignancy (i.e. missing 50 out of 5000 malignancies) for the cases detectable by screening mammography.

It should be noted that the current CAD systems were usually measured against a limited number of cancer cases and benign cases to determine an operating point or several operating points or CADe scores by the number of false positives per mammogram or number of false positives per case of 4 mammograms at the operating point. The operating points are typically set at a point where the total number of false positives of all abnormalities are approximately 2 per case of 4 mammograms. However, these cases are not large enough in number to provide meaningful or quantitative statistics for such thresholds as 2% probability of malignancy.

Figure 4:
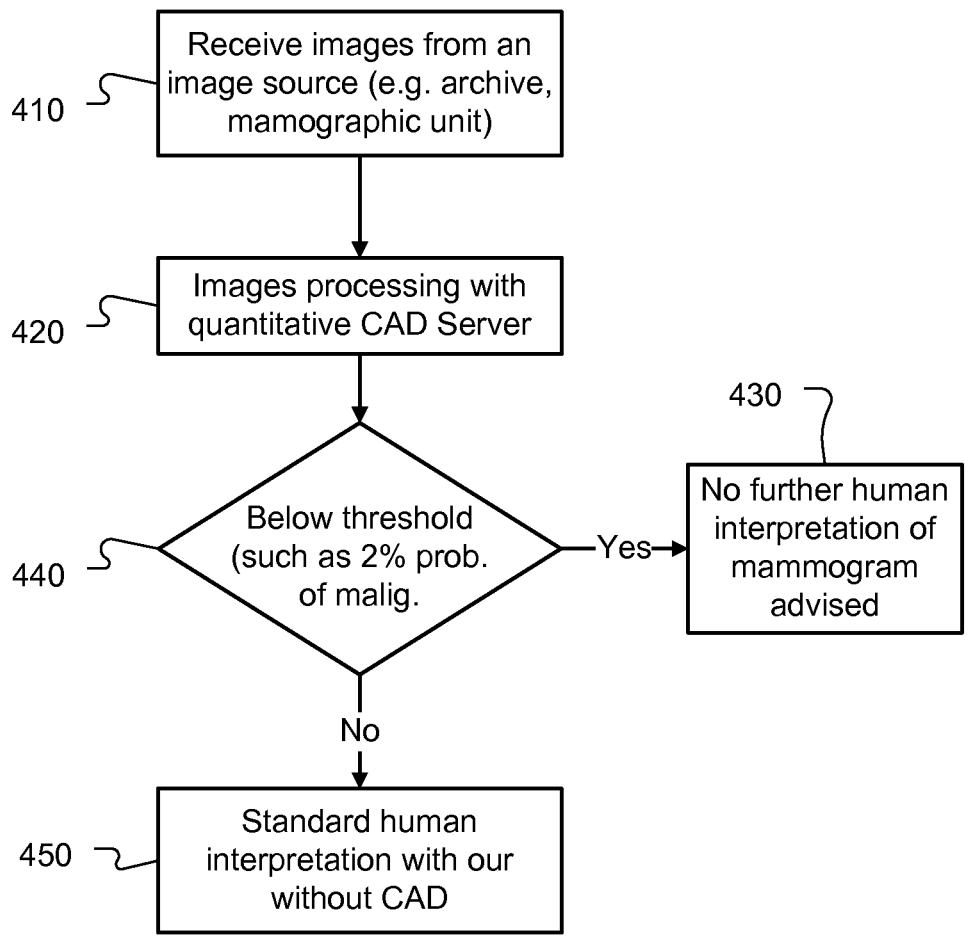
FIG. 4 is a flowchart showing steps in a triage system, according to some embodiments.

Although many of the embodiments described herein are directed to screening mammography with CAD prompting, according to other embodiments the techniques described herein are applied to a triage system in which the quantitative probability is applied to mammograms before any human interpretation. FIG. 4 is a flowchart showing steps in a triage system, according to some embodiments. In step 410, a source of mammograms, such as an archive or a mammography unit, supplies mammograms to a quantitative CAD server 420. In step 420, the mammograms, typically four per case, are processed through the quantitative CAD server. The decision is then made in step 430 using a threshold. According to some embodiments, the threshold is set for a calibrated 2% probability of malignancy. In step 440, if the mammogram, or a case of 4 mammograms, does not contain any lesions over a certain selected threshold, e.g. 2% probability of malignancy, the patient will be asked to return on the next scheduled screening visit and the mammograms will go into the archive and no further human interpretation will be needed. In Step 450, if the mammogram or set of mammograms contain one or more lesions over a certain selected threshold, e.g. 2% probability of malignancy, the mammograms will enter the standard human interpretation/reading process without CAD, or with CAD such as shown in FIG. 1 step 110. Since majority of the mammograms would not contain any lesions above the selected threshold, substantial cost savings, proportional to the percentage of mammograms triaged away from human interpretation, could thus be achieved.

Although many of the embodiments described herein are directed to screening mammography, according to other embodiments the techniques, including the triage system, described herein are applied to other medical screening procedures. According to one embodiment, the techniques herein are applied to other radiological imaging screening examinations such as CT lung scans for lung cancer screening purposes and other non-x-ray imaging screening examinations for breast cancer.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A method of interactively displaying computer aided detection results of screening mammogram images comprising:
   receiving first and second digitized screening mammogram images of a breast tissue, the first and second images resulting from separate image captures of the breast tissue;
   processing the first and second images with a processing system using one or more computer aided detection algorithms thereby generating computer aided detection results, wherein the computer aided detection results include one or more computer identified regions of interest identified by the one or more algorithms as possibly relating to an abnormality;
   displaying the first digitized image to a user;
   receiving from the user a location on the first image of a user identified region of interest, which is identified by the user as possibly relating to malignancy in the breast tissue;
   displaying to the user, in response to the received location from the user, a numerical value of a probability that the user identified region of interest is malignant based on the computer aided detection results, wherein the numerical value of the probability is calculated by the processing system using the one or more computer aided detection algorithms that are quantitatively calibrated using at least 1000 test images known to include a malignancy;
   displaying the second image simultaneously with the first image;
   automatically, in response to the received location from the user, calculating with the processing system a region of interest in the second image that corresponds to the user identified region of interest in the first image;
   automatically visibly highlighting on the second image the corresponding region of interest in the second image; and
   displaying the computer aided detection results such that computer identified regions of interest that correspond to user identified regions of interest are not highlighted to the user which reduces effort by the user in cases where a user identified region of interest corresponds to a computer identified region of interest.

2. A method of interactively displaying computer aided detection results of screening mammogram images comprising:
   receiving first and second digitized screening mammogram images of breast tissue, the first and second images resulting from separate image captures of the breast tissue;
   processing the first and second images with a processing system using one or more computer aided detection algorithms thereby generating computer aided detection results including one or more computer identified regions of interest identified by the one or more algorithms as possibly relating to a malignancy;
   displaying the digitized first image to a user;
   receiving from the user a location of at least one user identified region of interest identified by the user as possibly relating to a malignancy;
   displaying to the user, in response to the received location from the user, information on the first image indicating a likelihood that the user identified region of interest is malignant based on the computer aided detection results;
   displaying the second image simultaneously with the first image;
   automatically, in response to the received location from the user, calculating with the processing system a location in the second image that corresponds to the user identified region of interest in the first image;
   automatically visibly highlighting on the second image the corresponding location in the second image when the second image corresponds to a computer identified region of interest; and
   after the user finishes identifying regions of interest, displaying one or more computer identified regions of interest based on the computer aided detection results that are associated with a probability of malignancy above a predetermined threshold value and that do not correspond to any regions of interest previously identified by the user, thereby reducing effort by the user.

3. A method according to claim 2 further comprising calculating from the computer aided detection results a probability that each of the one or more computer identified regions of interest is a malignancy based at least in part on a calibration procedure including a number of test images known to include an abnormality.

4. A method according to claim 3 wherein the number of test images is at least 1000.

5. A method according to claim 3 wherein the information displayed to the user on the first image indicating a likelihood of malignancy includes a numerical value of the probability that the user identified region of interest is malignant.

6. A method according to claim 2 wherein the information displayed to the user on the first image indicating a likelihood of malignancy includes a graphical indicator of the probability that the user identified region of interest is malignant.

7. A system for interactively displaying computer aided detection results of screening mammogram images comprising:
   a processing system adapted and programmed to receive first and second digitized screening mammogram images of a breast tissue, the first and second images resulting from separate image captures of the breast tissue, and to process the first and second images using one or more computer aided detection algorithms thereby generating values relating to likelihood of an abnormality for a plurality of computer identified regions of interest; and
   an interactive displaying system adapted to display the first digitized image to a user, to receive from the user a location of a user identified region of interest, which is identified by the user as possibly relating to an abnormality in the breast tissue, to display to the user, in response to the received location from the user, information on the first image indicating the likelihood of an abnormality of the user identified region of interest, displaying the second image simultaneously with the first image, in response to the received location from the user, automatically visibly highlighting on the second image a region of interest in the second image that corresponds to the user identified region of interest, and after the user finishes identifying regions of interest, displaying one or more of the computer identified regions of interest that do not correspond to any regions of interest previously identified by the user, thereby reducing effort by the user.

8. A system according to claim 7 wherein the processing system is further programmed to relate the values relating to likelihood of an abnormality to probabilities of an abnormality.

9. A system according to claim 8 wherein the relating is based at least in part on a calibration procedure including a number of test images known to include an abnormality.

10. A system according to claim 9 wherein the number of test images is at least 1000.

11. A system according to claim 10 wherein the number of test images is at least 5000.

12. A system according to claim 7 wherein the processing system performs sufficient processing of the first and second images prior to the displaying of the first and second digitized images to the user, such the information indicating the likelihood of an abnormality can be displayed in real-time to the user in response to the received location of the user identified region of interest.

13. A system according to claim 7 wherein the information displayed to the user indicating the likelihood of an abnormality includes a numerical indicator of a probability that the user identified region of interest is a malignancy.

14. A system according to claim 7 wherein the information displayed to the user indicating the likelihood of an abnormality includes a graphical indicator of a probability of an abnormality corresponding to the user identified region of interest.

15. A system for interactively displaying computer aided detection results of screening mammogram images comprising:
a processing system adapted and programmed to receive a digitized screening image of a breast tissue, to process the image using one or more computer aided detection algorithms thereby generating computer aided detection results including one or more computer identified regions of interest identified by the one or more algorithms as possibly being malignant, and to calculate from the computer aided detection results a numerical value of a probability that the user identified region of interest is malignant wherein the calculation has been quantitatively calibrated using at least 1000 test images known to include a malignancy; and
an interactive display system adapted to display the digitized image to a user, to receive from the user a location of at least one user identified region of interest identified by the user as possibly being malignant, to display the numerical value of probability, and after the user finishes identifying regions of interest, to display the computer identified regions of interest that are associated with a probability of malignancy above a predetermined threshold value and that do not correspond to any regions of interest previously identified by the user, thereby reducing effort by the user.

16. A system according to claim 15 wherein the display system is further adapted to display to the user in real-time, in response to the received location from the user, the numerical value of probability.

17. A system according to claim 15 wherein the display system is further adapted display to the user a graphical indicator of the probability that the user identified region of interest is malignant.

18. A system according to claim 15 wherein the display system is further adapted to display simultaneously with the digitized image, a second digitized screening image of the breast tissue, and the processing system is further programmed to process the digitized image and the second digitized image such that the display system can automatically highlight on the second image a location corresponding to the received location of the user identified region of interest.

19. A method of interactively displaying computer aided detection results of screening mammogram images comprising:
receiving first and second digitized screening mammogram images of a breast tissue, the first and second images resulting from separate image captures of the breast tissue;
processing the first and second images with a processing system using one or more computer aided detection algorithms thereby generating a plurality of computer identified regions of interest;
calculating with the processing system using a calibrated process, for each computer identified region of interest, a numerical value of a probability that the computer identified region of interest is malignant, wherein the calibrated process has been calibrated using at least 1000 test images known to include a malignancy;
displaying the first digitized image to a user;
receiving from the user a location on the first image of a user identified region of interest, which is identified by the user as possibly relating to malignancy in the breast tissue;
displaying to the user, when the received location from the user corresponds to a computer identified region of interest, the numerical value of a probability that the computer identified region of interest is malignant;
displaying the second image simultaneously with the first image;
automatically, in response to the received location from the user, determining with the processing system whether a computer identified region of interest in the second image exists that corresponds to the user identified region of interest in the first image;
automatically visibly highlighting on the second image, if determined, the computer identified region of interest in the second image that corresponds to the user identified region of interest in first image; and
after the user finishes identifying regions of interest, displaying one or more of the computer identified regions of interest that are associated with a probability of malignancy above a predetermined threshold value and that do not correspond to any regions of interest previously identified by the user, thereby reducing effort by the user.

* * * * *